United States Patent [19]

Swajger et al.

[11] Patent Number: 5,601,567
[45] Date of Patent: Feb. 11, 1997

[54] METHOD OF SIZING A FEMORAL CANAL USING A MODULAR FEMORAL TRIAL HIP REPLACEMENT SYSTEM

[75] Inventors: Glenn Swajger, Wayne; Thomas J. Parchinski, Wanaque, both of N.J.

[73] Assignee: Howmedica Inc., N.Y., N.Y.

[21] Appl. No.: 630,895

[22] Filed: Apr. 3, 1996

Related U.S. Application Data

[62] Division of Ser. No. 268,472, Jun. 30, 1994.
[51] Int. Cl.$^6$ ................................................. A61B 17/56
[52] U.S. Cl. ........................................... 606/102; 606/86
[58] Field of Search ............................. 606/102, 89, 86, 606/79, 99, 100, 62, 53; 623/23, 22, 16, 18, 66

[56] References Cited

U.S. PATENT DOCUMENTS 5,100,407 3/1992 Conrad et al. .......................... 606/79

Primary Examiner—Guy V. Tucker
Attorney, Agent, or Firm—Pennie & Edmonds

[57] ABSTRACT

A multi-piece trial femoral component kit for use in sizing a femoral cavity prior to implantation of a prosthetic femoral implant. The trial femoral component kit has at least two distal trial components of different size and two proximal trial components of different size and mating elements which allow the proximal and distal components to be releasably coupled to form a femoral trial prosthesis. The distal trial component combines with the proximal trial component to form the stem of the femoral trial prosthesis, the joint of the two components located in the circumferential area between the gluteal tuberosity and about 2" below the pectineal line of the femur when the femoral trial is inserted within the femur. The distal and proximal components may further include means for selectively combining the proximal and distal components to form a femoral trial prosthesis that corresponds to an available prosthetic femoral implant. The dimensions of the distal and proximal components may be undersized when compared to the corresponding regions of the prosthetic femoral implant.

22 Claims, 3 Drawing Sheets

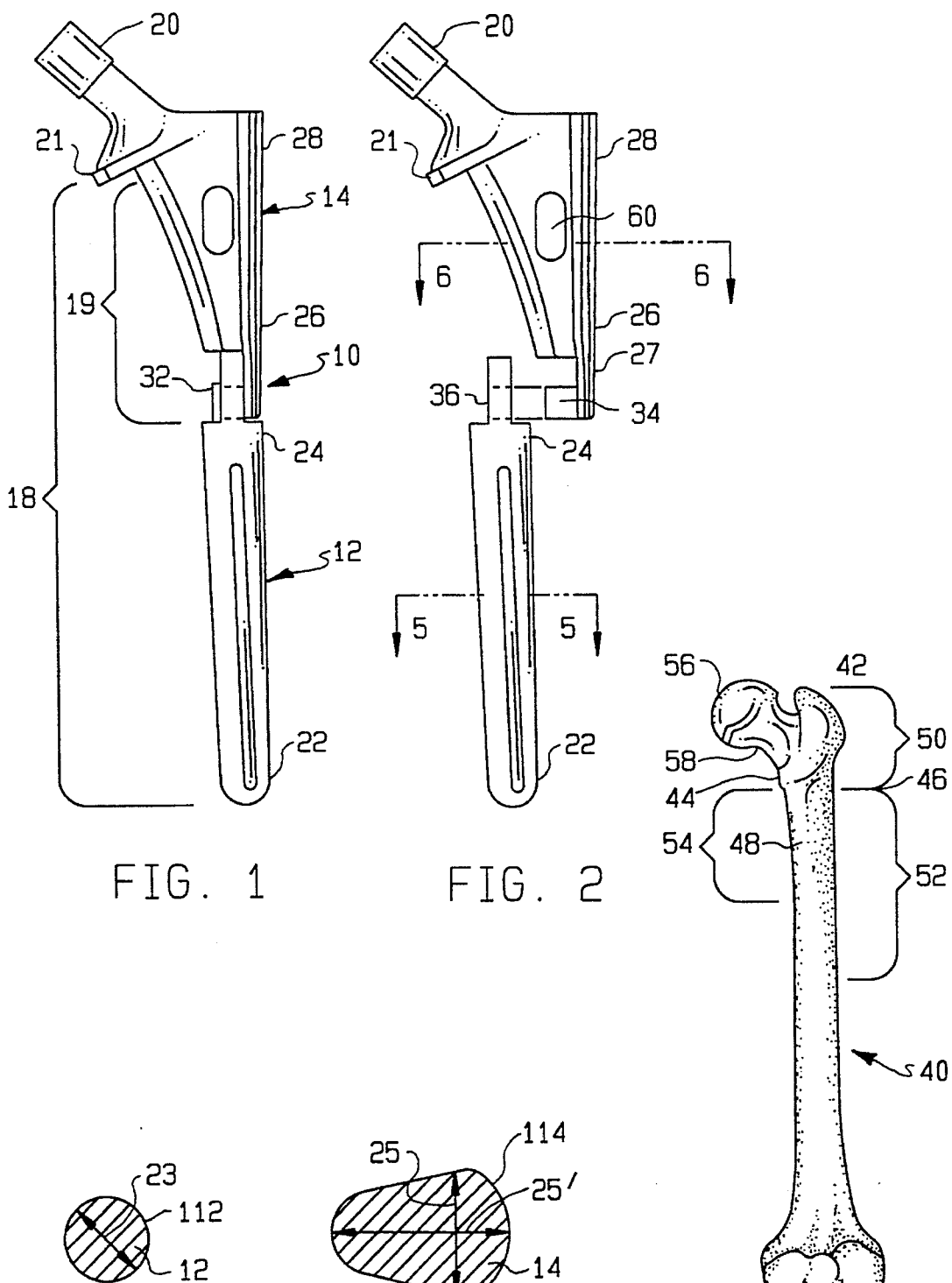

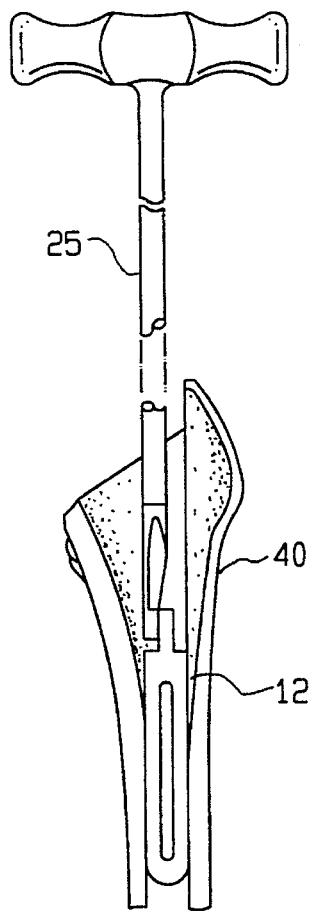 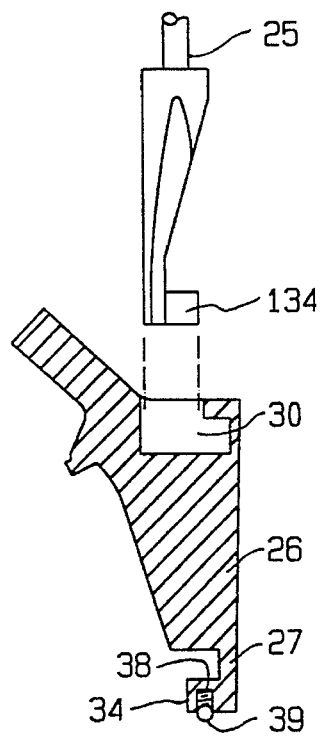 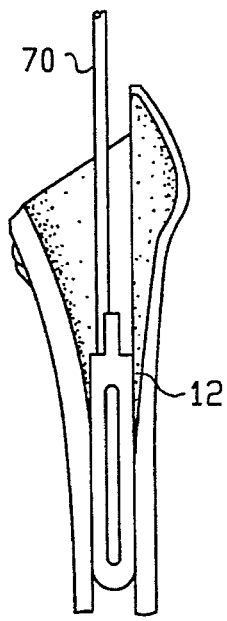 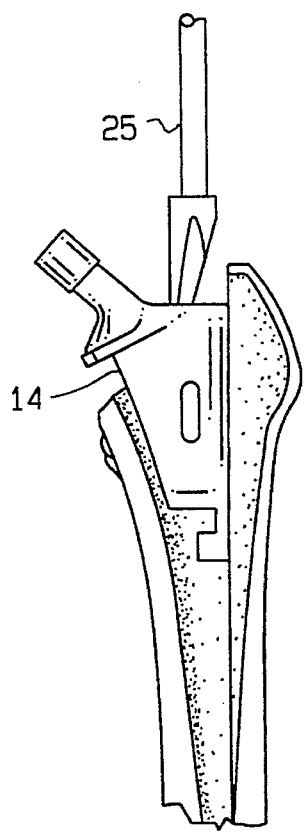
FIG. 7
FIG. 9
FIG. 8
FIG. 10

METHOD OF SIZING A FEMORAL CANAL USING A MODULAR FEMORAL TRIAL HIP REPLACEMENT SYSTEM

This is a division of application Ser. No. 08/268,472, filed Jun. 30, 1994, still pending.

BACKGROUND OF THE INVENTION

1. Field of the Invention

This invention relates to an orthopedic trial femoral component for use in determining the correct prosthetic femoral component for implantation from a group of prosthetic femoral components. More particularly, this invention relates to a two-piece trial component to be used as a guide for the surgeon in selecting the proper sized prosthetic femoral component.

2. Description of the Prior Art

Orthopedic surgery to replace a femur head and neck with a prosthetic component or to replace a previously implanted femoral prosthetic device is a complex operation requiring a relatively lengthy surgery. There has been a need to shorten and simplify this procedure while simultaneously providing the best fit between the prepared femoral canal and the prosthetic implant. This is especially true since many of the patients requiring such surgery are elderly or multi-trauma patients who require a series of operations and the longer the patient is under anesthesia, the greater the risk.

To determine the appropriate femoral implant size, the surgeon takes and examines X-rays of the femur. He then uses a trial component as a guide in preparing the femur to receive the chosen prosthesis. The surgeon attempts to select a trial implant which fits so that his final implant will likewise fit.

In the past, surgeons have used a series of one-piece trial prostheses which were identical in size to corresponding prosthetic implants. These prosthetic femoral implants came in discrete sizes which had been determined to cover the widest range of patients that surgeons were likely to encounter.

The surgeon would prepare the femoral canal by rasping and/or reaming and through guesswork, he would determine if the one-piece femoral trial prosthesis fit. Difficulties were encountered with a one-piece femoral trial-prosthesis because the proximal body of the trial prosthesis blocked the view of the medullary canal and this made it difficult to determine the correct one-piece prosthesis. The surgeon, upon implementation, often found that either his preparation of the femur was incorrect or the geometry of the prepared femur did not allow for the preliminarily chosen femoral implant to be used. Often it was extremely difficult to discern whether the problem or obstruction was located distally around the stem or proximally around the body portion of the trial prosthesis.

Manufacturers compensated for these difficulties by providing a series of femoral prosthetic implants with identical stem lengths but different neck/body sizes or vice versa. The surgeon also was provided with a series of one-piece trial prostheses with multiple stem and body sizes. The surgeon then used trial and error methods to determine the best fitting trial prosthesis from the different trial prostheses.

To overcome this position, modular two-piece trial prostheses were developed such as disclosed in U.S. Pat. No. 5,100,407. The disclosed modular trial system provides a two-piece trial component kit with a plurality of interchangeable heads and stems. This two-piece trial prosthesis separates the head and neck region of the trial prosthesis from the stem portion to provide the surgeon with a cross-sectional view of the bone where the surgeon cuts the femur. With this two-piece trial system, the stem and proximal body components of the femoral trial prosthesis are fitted separately so that the surgeon can address each fit independently and more easily.

The two-piece trial prosthesis of U.S. Pat. No. 5,100,407 is particularly adapted for resection cases where the surgeon must remove the head and neck of the femur in order to replace it with a femoral implant. The surgeon prepares a bone bed for the proximal body component of the two-piece trial prosthesis by using the trial proximal component as a guide for the necessary proximal cut of the femur and/or to check the accuracy of his rough cut.

The surgeon then moves onto fitting the distal trial stem component by first inserting various trial stem sizes to see which fits the patient best. The surgeon can quickly access the stem fit because there is no proximal head and body to block his view so he can clearly see the stem within the femoral canal. In the one-piece system, it would not be possible to view the distal fit because the integral head/body would obstruct the surgeon's view.

In the described two-piece trial system, the trial prosthesis is composed of a stem component and a body component, thus the distal and proximal fit of the stem within the femoral canal is addressed by use of a single trial component. Therefore, it is not always possible to size the stem of the prosthesis both distally and proximally within the femoral canal. In revision cases, where a previous femoral implant is being replaced and the epiphysis of the femur is gone, it becomes increasingly important to fit the femoral canal with the implant along its entire length. Thus, there has been a need in the art for a trial prosthesis which adequately address the aforementioned difficulties and drawbacks of existing devices.

SUMMARY OF THE INVENTION

It is an object of the present invention to provide a two-piece trial femoral prosthesis to be used as a guide in determining the correct prosthetic femoral implant for implantation into a femur from a group of prosthetic femoral implants.

It is also an object of the present invention to provide a two-piece trial femoral prosthesis that allows the proximal and distal fit of the femoral canal to be accurately and independently performed.

It is a further object of the present invention to provide a two-piece femoral trial prosthesis that addresses proximal and distal fill of the femoral canal of the femur with different components so that the surgeon can select the correct prosthetic femoral implant for implantation into-the femur from a group of prosthetic femoral implants.

It is an object of the invention to provide a two-piece femoral trial prosthesis that separates the stem of the trial prosthesis into two separate components so that maximum interference between the implant along the length of the femoral canal can be achieved.

It is an object of the invention to provide a method of addressing both proximal and distal fill of the femoral canal by the use of combinable proximal and distal trial components having an area of intersection when inserted into the femur that corresponds to the metaphysis.

These and other objects are provided by the present invention which includes a multi-piece trial femoral component kit for use in sizing a femoral cavity prior to implantation of a prosthetic femoral implant. The trial component kit includes a number of different distal components and a number of different proximal components which are combinable to form numerous different-sized femoral trial prostheses. The distal and proximal trial components are coupled to produce a trial femoral prosthesis which can be used as a guide for correctly sizing the cavity within the femur for a prosthetic femoral implant.

Each distal portion and proximal component includes a mating element to couple the two pieces together. The combination of the distal trial component and proximal trial component together form the stem of a modular trial femoral prosthesis. The two components of the modular trial prosthesis couple in the stem of the trial prosthesis corresponding to the circumferential area on the femur between the gluteal tuberosity and about two (2) inches below the pectineal line, i.e., between the soft spongy bone of the epiphysis and the hard cortical bone of the metaphysis. The mating elements are configured so that the two-piece trial femoral prosthesis can be held together to form a one-piece unit but can be selectively separated so that more than one proximal component can be coupled to each distal component or vice versa.

The present invention uses a variety of proximal stem geometries that are independent of the various distal stem geometries. With this unique separation of the stem of the trial prosthesis, and the various distal and proximal stem geometries available, proximal and distal fit of the femoral canal can be evaluated independently, i.e., the distal stem portion separate from the proximal stem portion, so that an implant can be selected that captures maximum interference along the length of the femoral canal.

Each mating element can be provided with a key or keyway shaped to allow selected proximal components to be coupled to selected distal components to ensure that the surgeon can only form a two-piece trial prosthesis which corresponds to an actual prosthetic femoral implant.

The femoral trial prosthesis may be undersized so that minimal resistance of the trial within the prepared femur will ensure a proper fit of the femoral implant. The distal trial component may have a diameter that is approximately 0.75 mm smaller than the corresponding portion of the actual implant while the proximal trial component may have a diameter that is approximately 1.0 mm smaller than the diameter of the corresponding portion of the actual implant.

These and other objects and advantages of the present invention will become apparent from the following description of the accompanying drawings.

BRIEF DESCRIPTION OF THE DRAWINGS

Similar reference characters in the drawings denote similar elements through the views:

FIG. 1 is an elevational view of a two-piece modular femoral trial prosthesis of the present invention;

FIG. 2 is an elevational view of an uncoupled two-piece modular femoral trial prosthesis of the present invention;

FIG. 4 is the dorsal view of the right femur;

FIG. 5 is a cross-sectional view of the distal femoral component of FIG. 2 taken along line 5—5;

FIG. 6 is a cross-sectional view of the proximal femoral component of FIG. 2 taken along line 6—6;

FIG. 7 is a cross-section of a resected femur receiving the distal component of the trial prosthesis of the present invention coupled to the trial positioner handle;

FIG. 8 is a cross-section of a resected femur with the distal component of a trial prosthesis of the present invention being retrieved by a retrieval hook;

FIG. 9 is a cross-section of the proximal component of a trail prosthesis and a distal end of a trial positioner handle of the present invention; and FIG. 10 is a cross-section of a resected femur with the proximal component of the trial prosthesis of the present invention coupled to the trial positioner handle.

DETAILED DESCRIPTION OF THE INVENTION

Figure 3:
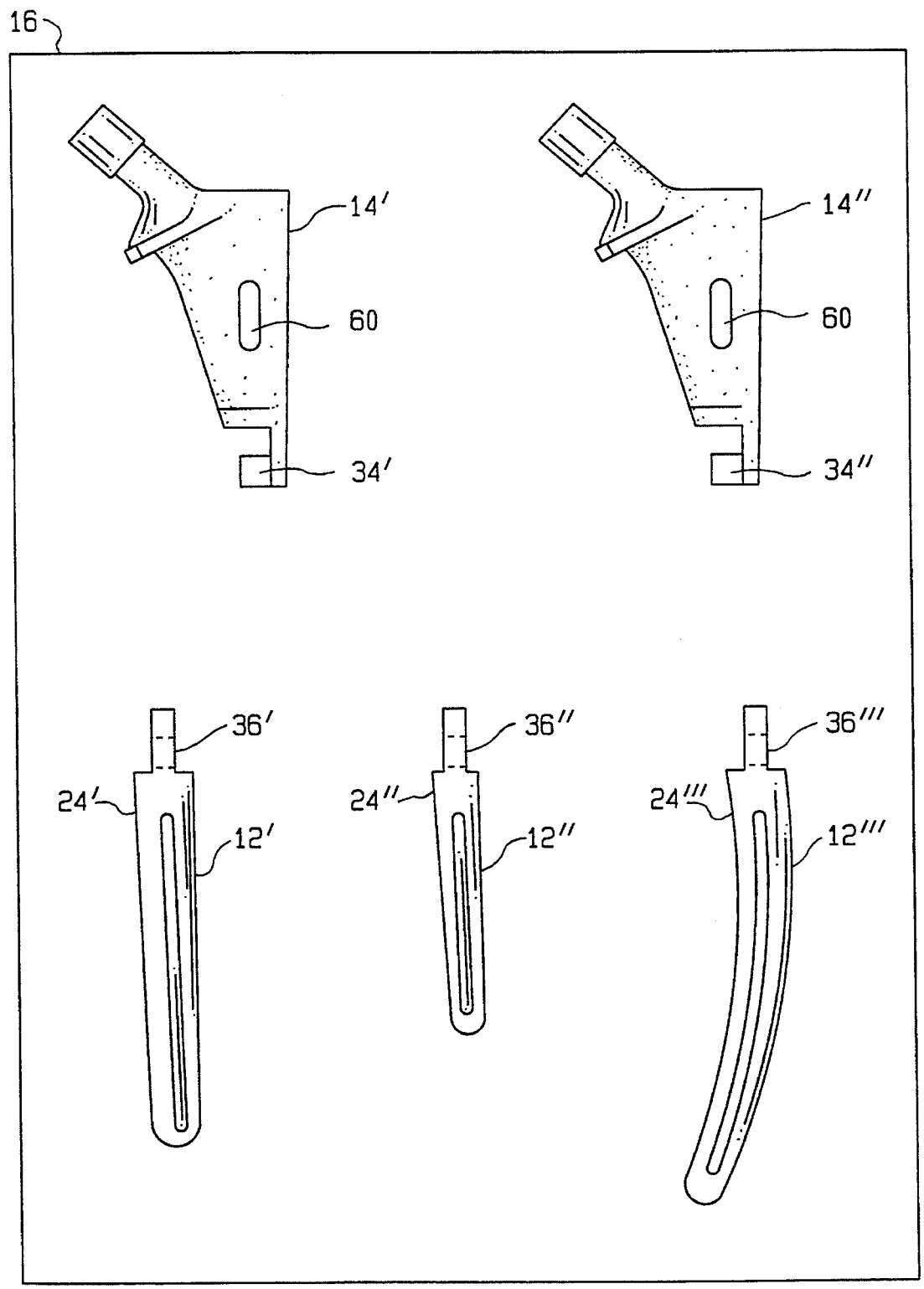
FIG. 3 is an illustration of a modular trial component kit of the present invention.

Referring to FIGS. 1 and 2, there is shown the two-piece trial femoral prosthesis of the present invention generally denoted as 10. Trial femoral prosthesis 10 is composed of a distal trial component 12 coupled to a proximal trial component 14. Distal trial component 12 has a distal portion 22 that is received in the prepared femoral canal 140 (see FIG. 8) and a proximal portion 24 that couples with the distal portion 26 of the proximal trial component 14. A proximal portion 28 of the proximal trial component 14 includes a flange or collar 21 that butts against and rests on the bone where the surgeon resected the femur, a trunion 20 which is used to mount a spherical ball (not shown) and an opening 30 (shown in FIG. 7) to receive a trial positioner handle 25.

The trial femoral prosthesis 10 represents the combination of a distal trial component 12 and a proximal trial component 14 which may be formed from a multi-piece trial femoral component kit 16. Referring to FIG. 3, the multi-piece trial femoral component kit 16 may include, for example, a number of different distal trial components 12', 12'', 12''', and a number of different proximal trial components 14', 14''. These can be combined to form numerous different-sized femoral trial prostheses 10.

The distal trial components may vary, for example, in diameter, length and geometry. FIG. 5 shows a cross-section 112 of distal component 12 with a diameter 23. It being understood that the cross-sectional shape shown in FIG. 5 is representative and that various cross-sectional shapes are possible. The distal trial components, for instance, may vary from 12.5 mm to 21.5 mm in 1.5 mm diameter increments, may be 180 mm or 250 mm in length and may be bowed or straight in configuration. The bowed distal trial components can be assembled to create a right or left trial prosthesis. Referring to FIG. 3, there is illustrated distal trial component 12', 12'', which are both straight and of the same length but vary in diameter. Distal trial component 12''', is bowed and is longer than either distal components 12', or 12''.

The proximal trial components 14', 14'', vary proximally in neck length of the femur, collar width as well as proximal calcar area geometry. The neck length of the femur is varied by changing the length of the trunion 20 while the collar width refers to changes in the size of the lip created by collar 21. The proximal calcar area refers to the proximal stem 19 on proximal component 14 which begins at a location just below the collar 21 and extends to the distal end 27 of the proximal component 14. The proximal calcar area of the different proximal components 14 vary in cross-sectional area and length.

FIG. 6 shows a cross-section 114 of proximal component 14 with a diameter 25. It is to be understood that the term diameter as used herein is used to refer to the width of both circular and non-circular cross-sections of distal and proximal components 12, 14 and is illustrated in FIGS. 5 and 6 as 23, and 25, 25'. It again being understood that the cross-sectional area shown in FIG. 6 is for illustrative purposes and that various cross-sectional shapes of the proximal stem 19 are possible.

The length of the proximal components 14 are varied with the proximal calcar geometry so that the proximal components 14 extend to roughly the same area when inserted within the prepared femoral canal 140. In this manner, a proximal component 14 with a larger cross-sectional site at a point just distal to the collar 21 will have a longer length so that the distal end 27 of the proximal component 14 will extend deep enough into the patient's prepared femoral canal 140. Representative lengths of the proximal stem 19 are approximately 40–50 mm. Multiple other variations in proximal component 14 will be apparent to persons of ordinary skill in the art.

The contents of a preferred trial kit of the present invention include eighteen (18) total pieces with seven (7) straight distal trial components of 180 mm in length, seven (7) bowed distal trial components of 250 mm in length and three (3) proximal trial components. These eighteen (18) components allow the surgeon to construct forty-two (42) combinations of monolithical femoral implants. The distal trial components 12 vary from about 12.5 mm to about 21.5 mm in diameter, preferably in about 1.5 mm increments. Proximally the trial components 14 vary in neck length of the femur, collar width as well as proximal calcar area geometry. Of course, these combinations can be multiplied by adding different distal and/or proximal trial components.

When the trial femoral prosthesis 10 of the present invention is fitted within the femur, the joint 32 between the distal and proximal trial components 12, 14 is located in the metaphysis 52 of the femur 40 (see FIG. 4) or more specifically the circumferential area 54 between the gluteal tuberosity 46 and about two inches (2") below the pectineal line 48. The area of intersection is the area between the soft spongy bone of the epiphysis 50 and the hard cortical bone of the metaphysis 52 or an area approximately half-way into the metaphysis 52 of the femur.

The combination of the distal trial component 12 with the proximal trial component 14 together form the stem 18 of the trial femoral prosthesis 10. In other words, the stem 18 of the trial femoral prosthesis 10 is composed of two separate pieces. In particular, the stem 18 of the trial prosthesis 10 is formed by the combination of the proximal stem 19 of the proximal trial component 14 with the distal trial component 12. In this manner, the stem 18 of the trial prosthesis 10 which is inserted into the femoral canal of the femur 40 can be independently and separately sized both distally and proximally by the distal and proximal trial femoral components 12, 14.

By having different-sized and geometrically-shaped distal and proximal trial components 12, 14 available, and by independently selecting different proximal and distal components 12, 14 to form the stem 18 of the trial prosthesis 10, the surgeon can choose the best size monolithical femoral implant that will maximize distal-to-proximal interference of the medullary canal. The ability to maximize the fit of the stem of the femoral implant within the femoral canal is particularly important in revision surgical procedures where a previous femoral implant is to be replaced and the epiphysis 50 of the femur 40 has been removed.

The femoral trial prosthesis 10 may be undersized when compared to the prosthetic femoral implant so that minimal resistance upon fitting the trial prosthesis 10 will ensure that the femoral implant will make contact with the bone. Accordingly, the cross-sections of the distal and the proximal trial components 12, 14 in the trial kit 16 must be undersized when compared to the respective distal and proximal regions of the implant to which the distal and trial components correspond. The distal trial component 12 may have a diameter 23 that is approximately 0.5 to 1.25 mm, and preferably 0.75 mm, smaller than the corresponding diameter of the implant and the proximal trial component 14 may have a diameter 25 that is approximately 0.5 to 1.25 mm, and preferably 1.0 mm, smaller than the corresponding diameter of the actual femoral implant. It is to be understood that the distal and proximal components 12, 14 can be undersized by varying amounts, i.e., 0.5 to 1.25 mm, along their respective lengths.

At distal end 27 of proximal trial component 14 is a male element 34 which is adapted to be inserted within a corresponding opening 36 (not shown) in the proximal end 24 of distal femoral component 12. The male element 34 and opening 36 are preferably a square-drive socket combination and preferably of ⅜" size, although other socket configurations are equally useful. In the square drive combination, as shown in FIG. 7, the male element 34 is provided with a spring 38 and detent ball 39 designed to selectively, releasably and repeatably couple distal trial component 12 to proximal trial component 14. The ball 39 is depressed as male element 34 is slid within corresponding opening 36 and then springs out, locking the components together, upon reaching a predetermined point. The spring 38 is sized so that a predetermined amount of hand pressure tending to separate proximal trial component 14 from distal trial component 12 depresses the ball 39 and allows the two-piece trial prosthesis to be uncoupled. It is understood that the respective male element 34 and opening 36 may be reversed or any other coupling mechanism may be utilized that allows the distal trial component 12 and proximal trial component 14 to be selectively, releasably, and repeatably connected.

Because implant manufacturers only supply a discrete number of femoral implants, it is necessary to ensure that the surgeon only chooses a proximal and distal component 12, 14 that couple to form a trial prosthesis 10 that corresponds to an actual implantable prosthesis.

In order to achieve this, the male element 34 or opening 36 may be provided with a key or keyway (not shown) sized to allow selected distal components 12 to be coupled to selected proximal components 14 so that only a two-piece trial prosthesis 10 can be formed that corresponds to an available femoral implant. A different way of preforming this same function is to provide a label 60 on the proximal trial component 14 which provides a list of the different distal components 12 that will couple with that proximal trial component 14 to form a trial prosthesis 10 which corresponds to an available femoral implant. Using the label method requires the surgeon to check that the combination of distal and proximal components 12, 14 used correspond to an available femoral implant.

The process of utilizing the trial component kit 16 of the present invention will now be described. Initially, the surgeon is supplied with a series of proximal trial components 14', 14", etc., from the kit 16, one corresponding in size to each size stem/body portion of an implantable prosthesis. Likewise, the surgeon is supplied with a group of distal trial components 12', 12", 12'", etc., from the kit 16, one corresponding in size to each distal stem portion provided on an implantable prosthesis. With the modular trials of the present invention, the surgeon can begin the procedure with attention to either proximal or distal fit.

In the case of revision surgery, the failed femoral prosthesis and cement should first be removed. Thereafter, and in the case of rejecting the femur, the surgeon then prepares for the osteotomy. The appropriate broach is laid against the femur at the point where the medial aspect of the broach lies slightly distal to the most distal medial bone loss. The osteotomy can be marked off the broach with methylene blue. The surgeon makes the osteotomy in line with the angle of the broach. The broach can be used as a cutting surface.

In most revision cases, the surgeon can very clearly access the distal femoral canal. If, however, the technique used to implant the previous femoral component did not open the medial aspect of the greater trochanter 42 (see FIG. 4), the surgeon should precede distal reaming by opening this area of the proximal bone. The surgeon should have straight-line access to the distal femoral canal.

The surgeon can now prepare the distal femoral canal for the distal trial component 12. The femoral canal should be enlarged by reaming to accept one of the available distal stem components 12. Reaming should extend into the femoral canal to a point distal to the full length of the anticipated implant. It is expected that in most cases involving the 250 mm length stem and in some cases involving the 180 mm length version, the distal canal will require at least about 1 mm of over-reaming.

At any time during the reaming process, the surgeon may insert the distal trial component 12 into the reamed canal to check the implant's ultimate fit. For these purposes trial handle positioner 25 is provided, which releasably attaches to the distal stem trial component 12. Referring to FIG. 5, a male mating element 134 which has the same configuration as male element 34 of proximal trial component 14 attaches to the distal trial component 12 in the same manner as mating element 34 of the proximal trial component 14.

The distal stem trial component 12 is undersized, preferably by approximately 0.75 mm in diameter as compared to the corresponding portion of the actual implant. Therefore, the distal trial component 12 trial should seat in the canal without much resistance. A distal trial component 12 that does encounter resistance indicates a tight fit of the implant within the femoral canal.

Referring to FIG. 6, a retrieval hook 70 is provided to retrieve the distal stem trial component 12 and pull it out of the femur 40 in the unlikely event that the distal trial component 12 slips down the femoral canal. When distal stem preparation is complete, the surgeon can focus on proximal bone preparation.

The proximal region of the revision femur usually experiences far more unpredictable bone loss than does the distal canal. Therefore, before beginning proximal bone preparation, the proximal trial component 14 is inserted in order to access the potential fit of the trial. The same trial handle positioner 25 that is used with the distal stem component 12 is used with the proximal trial component 14. Trial handle positioner 25 fits within opening 30 in order to couple with proximal trial component 14. Mating element 134 of the trial handle positioner 25 couples with the proximal component 14 in opening 30 in the same manner as mating element 34 couples with opening 36 in the distal trial component 12.

Regardless of whether or not the modular proximal trial component 14 is used before proximal bone preparation, both midshaft reamers and broaches should be used to prepare the proximal area of the femur 40. Seating of proximal trial component 14 should be attempted periodically throughout bone preparation. The proximal trial component 14 is undersized approximately 1.0 mm compared to the dimensions in the corresponding region of the implant. The proximal trial component 14 therefore should offer little resistance.

The surgeon who has completed distal stem preparation should ensure that the chosen proximal trial component 14 couples with the distal trial component 12 already reamed and fitted to form a trial femoral prosthesis 10 that corresponds to an available implant and vice versa for the surgeon who prepares the proximal portion of the femur first.

The modular trial components 12, 14 can be assembled to perform the final trial reduction. The surgeon places the trial prosthesis 10 in the femur 40 and if the trial prosthesis 10 seats with minimum resistance, the corresponding implant will make proper contact with the bone upon implantation. The trial handle positioner 25 can be inserted into the proximal trial component 14 to make manipulation of the trial prosthesis 10 easier. If the modular trial components 12, 14 were used during bone preparation, it is unlikely that any difficulties will occur while inserting the trial prosthesis 10. If any resistance is experienced as the trial prosthesis 10 is inserted, the surgeon should redo the broaching and reaming steps of the bone preparation. Plastic heads are placed on the trunion 20 to complete the trial reduction. The surgeon may even desire to take interoperative X-rays to judge the fit and alignment of the trial prosthesis. The modular trial prosthesis 10 is removed upon verifying the fit and the corresponding one-piece implant is implanted within the femur using known techniques.

While the present invention has been described in its essentials, and by illustrative examples, those skilled in the art can appreciate that many changes and modifications may be made without departing from the spirit and scope of the present invention.

We claim:

1. A method of sizing a femoral canal of a resected femur of a patient for proximal and distal stem fit of a prosthetic femoral implant comprising:

(a) placing a distal trial component of a femoral trial component system within the femoral canal, said distal trial component having a distal and proximal end and being dimensioned and configured such that the proximal end is located between the soft spongy bone of the epiphysis and the hard cortical bone of the metaphysis of the femur when the distal end of the distal trial component is seated within the femoral canal;

(b) sizing the distal stem portion of the femoral canal by comparison with the distal trial component;

(c) placing a proximal trial component of said femoral trial component system within the femoral canal, said proximal trial component having a distal and proximal end and dimensioned and configured such that the distal end extends into the area between the soft spongy bone of the epiphysis and the hard cortical bone of the metaphysis;

(d) sizing the proximal stem portion of the femoral canal by comparison with the proximal trial component;

(e) combining the distal and proximal trial components to form a femoral trial member; and (f) placing the combined femoral trial member within the femoral canal and checking the fit of the femoral trial member within the femoral canal to ensure proper fit of the implant.

2. The method of claim 1 further comprising implanting a corresponding prosthetic femoral implant that has larger dimensions than the fitted femoral trial member.

3. The method of claim 2 further comprising implanting a corresponding prosthetic femoral implant having distal and proximal portions wherein the dimensions of the distal and proximal portions are larger by different amounts than the corresponding proximal and distal trial components of the selected femoral trial member.

4. The method of claim 1 further comprising securing the distal trial component to a handle and manipulating said component in the femoral canal with said handle.

5. The method of claim 4 further comprising securing the combined femoral trial member to said handle and manipulating it within the femoral canal with said handle.

6. The method of claim 1 further comprising securing the proximal trial component to a handle and manipulating said proximal component in the femoral canal with said handle.

7. The method of claim 1 further comprising providing a multi-piece trial femoral kit having at least two distal trial stem components of different size, at least two proximal trial components of different size, said proximal components being repeatably attachable to said distal components to form a femoral trial member.

8. The method of claim 1 wherein the distal trial component is dimensioned and configured such that its proximal end is located in the circumferential area between the gluteal tuberosity and about two inches (2") below the pectineal line of the femur when the distal end of the distal trial component is placed within the femoral canal and the proximal trial component is dimensioned and configured such that its distal end extends into the circumferential area between the gluteal tuberosity and about two inches (2") below the pectineal line of the femur when the proximal trial component is placed within the femoral canal.

9. Method for fitting a femoral canal with a prosthetic femoral implant comprising:

(a) providing a multi-piece trial femoral component kit comprising at least two distal trial components of different sizes and dimensions; at least two proximal trial components of different size and dimensions; and means for releasably connecting said proximal trial components to said distal trial components to form a femoral trial member having a stem for insertion into the femoral canal, the trial member having a predetermined dimensional relationship to a prosthetic femoral implant; wherein each said distal and proximal trial components have distal and proximal ends and predetermined lengths such that the connection between the distal and proximal trial components is located within the metaphysis of the femur when the femoral trial member is seated within the femoral canal and the stem of the femoral trial is formed by the combination of one of the distal trial components with one of the proximal trial components;

(b) inserting one of the distal trial components within the femoral canal and sizing the distal stem portion of the femoral canal by comparison with the distal trial component;

(c) inserting one of the proximal trial components within the femoral canal and sizing the proximal stem portion of the femoral canal by comparison with the proximal trial component;

(d) combining the selected distal and proximal trial components to form a femoral trial member; and (e) inserting the femoral trial member within the femoral canal and checking the fit of the femoral trial member within the femoral canal.

10. The method of claim 9 wherein the predetermined lengths of the distal and trial components is such that the connection between the distal and proximal components is located in the circumferential area between the gluteal turbosity and about two inches (2") below the pectineal line of the femur when the femoral trial member is fitted within the femoral canal.

11. The method of claim 9 wherein the predetermined dimensional relationship between the femoral trial member and the femoral implant is such that the dimensions of the proximal trial component are smaller than the dimensions of the corresponding portion of the femoral implant.

12. The method of claim 9 wherein the predetermined dimensional relationship between the femoral trial member and femoral implant are such that the dimensions of the distal and proximal trial components are smaller than the dimensions of the corresponding portions of the femoral implant.

13. The method of claim 12 wherein the predetermined dimensional relationship between the femoral trial member and femoral implant are such that the dimensions of the distal and proximal trial components are smaller by different amounts than the corresponding portions of the femoral implant.

14. The method of claim 12 wherein the diameter of the distal and proximal components are about 0.5 to 1.25 mm smaller than the corresponding diameter of the femoral implant.

15. The method of claim 13 wherein the diameter of the distal component is about 0.75 mm smaller and the diameter of the proximal component is about 1.0 mm smaller than the corresponding diameters or the femoral implant.

16. The method of claim 9 further comprising:

(a) providing a trial positioner handle having a proximal and distal end and means to repeatably and releasably attach the handle to the proximal or distal trial components;

(b) attaching the trial positioner handle to one of the distal trial components and using the trial positioner handle to insert the selected distal trial component within the femoral canal.

17. The method of claim 16 wherein the means for attaching the trial positioner handle to the distal or proximal trial component is the same as the means to couple the distal and proximal components together.

18. The method of claim 16 wherein the trial positioner handle is repeatedly attachable to the femoral trial member.

19. The method of claim 16 further comprising manipulating the distal trial component in the femoral canal with the handle.

20. The method of claim 9 wherein the trial component kit further comprises means for selectively combining the distal and proximal components to form a femoral trial member which corresponds to an available femoral implant.

21. The method of claim 9 further comprising:

(a) providing a retrieval hook; and (b) removing the distal trail component from the femoral canal by using the retrieval hook.

22. Method for sizing a femoral canal of a resected femur for a prosthetic implant comprising:

(a) providing a two-piece femoral trial member having a stem to be inserted into the femoral canal comprising a distal trial component having digital and proximal ends and predetermined dimensions; a proximal trial component having predetermined dimensions, a proximal end adapted to extend proximally from the femoral canal, a collar section adapted to rest on the femur and a distal end extending distally from the collar and adapted to be inserted into the femoral canal; means for connecting the proximal end of the distal trial component to the distal end of the proximal component to form the femoral trial member wherein the stem of the femoral trial member is formed by the combination of the distal end of the proximal trial component the distal trial component;

(b) inserting the distal trial component into the femoral canal and sizing the distal stem portion of the femoral canal by comparison with the distal trial component;

(c) inserting the distal end of the proximal trial component into the femoral canal until the collar section rests on the femur and sizing the proximal stem portion of the femoral canal by comparison with the proximal trial component;

(d) combining the proximal and distal trial components to form the femoral trial member; and (e) inserting the femoral trial member within the femoral canal and checking the fit of the stem of the femoral trial member within the femoral canal.

* * * * *

UNITED STATES PATENT AND TRADEMARK OFFICE
CERTIFICATE OF CORRECTION

PATENT NO. : 5,601,567

DATED : February 11, 1997

INVENTOR(S) : SWAJGER et. al.

It is certified that errors appear in the above-identified patent and that said Letters Patent is hereby corrected as shown below:

In Claim 15, Column 10 line 32, change "or" to "of".

In Claim 22, Column 10 line 64, change "digital" to "distal".

Signed and Sealed this

Twenty-ninth Day of April, 1997

Attest:

BRUCE LEHMAN

Attesting Officer

Commissioner of Patents and Trademarks